(12) United States Patent
Tigno, Jr.

(10) Patent No.: US 8,858,639 B2
(45) Date of Patent: Oct. 14, 2014

(54) SYSTEMS AND METHODS FOR CRANIAL IMPLANT ASSEMBLY ADAPTED FOR INSERTION DURING CRANIECTOMY PROCEDURE

(75) Inventor: Teodoro Aclan Tigno, Jr., Gaithersburg, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 13/812,274

(22) PCT Filed: Jul. 29, 2011

(86) PCT No.: PCT/US2011/045992
§ 371 (c)(1),
(2), (4) Date: Feb. 20, 2013

(87) PCT Pub. No.: WO2012/016200
PCT Pub. Date: Feb. 2, 2012

(65) Prior Publication Data
US 2013/0158670 A1    Jun. 20, 2013

Related U.S. Application Data

(60) Provisional application No. 61/369,403, filed on Jul. 30, 2010.

(51) Int. Cl.
*A61F 2/02* (2006.01)
*A61F 2/28* (2006.01)
*A61F 2/30* (2006.01)

(52) U.S. Cl.
CPC ......... *A61F 2/2875* (2013.01); *A61F 2002/305* (2013.01); *A61F 2002/30079* (2013.01); *A61F 2002/30179* (2013.01); *A61F 2310/0097* (2013.01); *A61F 2002/30909* (2013.01); *A61F 2002/30462* (2013.01); *A61F 2/30942* (2013.01)
USPC .................. 623/17.19; 623/17.17; 623/17.18

(58) Field of Classification Search
USPC .......... 623/17.18–17.19, 23.51–23.54; 703/1; 606/286
See application file for complete search history.

(56) References Cited

U.S. PATENT DOCUMENTS

| 4,014,319 A | 3/1977 | Favre |
| 4,026,276 A | 5/1977 | Chubbuck |

(Continued)

FOREIGN PATENT DOCUMENTS

| WO | 2007/146541 | 12/2007 |
| WO | 2009/085829 | 7/2009 |
| WO | 2012/082571 | 6/2012 |

OTHER PUBLICATIONS

Written Opinion of the International Searching Authority from PCT/US2011/045992, mailed Dec. 9, 2011.

(Continued)

*Primary Examiner* — Yashita Sharma
(74) *Attorney, Agent, or Firm* — MH2 Technology Law Group, LLP (57) ABSTRACT

Embodiments relate to systems and methods for a cranial implant assembly adapted for insertion during a craniectomy procedure. In aspects, the inventive cranial implant assembly can contain a peripheral attachment member for attachment to the edge of a skull opening, as well as an articulated spanning member that over-arches and holds a cover in place over the opening. The articulated spanning member contains a central implant fastened or connected to a swollen dura in the skull opening. As swelling of the dura subsides, tension is exerted on guidewires in both the spanning member and cover to draw those constructs into a rigid state. The tips of the spanning member can gradually approach the peripheral attachment member, and register into place using a locking mechanism, such as a pair of opposing magnets. As a result, only one surgical operation or procedure Is required to both perform a craniectomy and implant a supporting assembly for eventual skull regeneration.

20 Claims, 7 Drawing Sheets

(56) References Cited

U.S. PATENT DOCUMENTS

| | | | |
|---|---|---|---|
| 4,062,354 A | 12/1977 | Taylor et al. | |
| 4,281,667 A | 8/1981 | Cosman | |
| 7,655,047 B2 * | 2/2010 | Swords | 623/17.18 |
| 8,439,956 B2 * | 5/2013 | Ko | 606/281 |
| 2004/0010316 A1 * | 1/2004 | William et al. | 623/17.16 |
| 2005/0175703 A1 * | 8/2005 | Hunter et al. | 424/486 |
| 2008/0200954 A1 | 8/2008 | Tucci | |
| 2011/0028972 A1 | 2/2011 | Khanna | |

OTHER PUBLICATIONS

Supplementary European Search Report dated Jul. 2, 2014 from European Patent Application No. 11813283.6, pp. 1-5.

* cited by examiner

SYSTEMS AND METHODS FOR CRANIAL IMPLANT ASSEMBLY ADAPTED FOR INSERTION DURING CRANIECTOMY PROCEDURE

CROSS REFERENCE RELATED APPLICATION

This patent application claims priority to U.S. Provisional Application Ser. No. 61/369,403, filed Jul. 30, 2010, by the same inventor herein, which provisional application is incorporated in its entirety by reference herein.

FIELD

The present teachings relate to medical devices, and more particularly, to an initially non-rigid cranial implant introduced immediately during a craniectomy procedure that is capable of adapting to the shape of a displaced brain and of transitioning during the normalization of brain shape to a rigid state to protect the skull opening resulting from the procedure.

BACKGROUND OF RELATED ART

Several medical conditions including surgical interventions and trauma can lead to increasing intracranial pressure. These conditions include, but are not limited to: "malignant" cerebral infarction (stroke), brain tumors, epilepsy surgery, and craniosynostosis (congenital cranial anomalies), and brain injury trauma. In the case of brain injury trauma and/or strokes, these medical conditions can lead to a very dangerous effect of causing swelling or edema of brain matter and the enveloping dura within the confines of the cranium. The increased intracranial pressure caused by these conditions is be associated with serious complications including bruising or other damage to brain tissue, delirium, loss of consciousness or cognitive functions, secondary cerebral ischemia or infarctions, brain herniation and possibly death, if left untreated. This situation typically can only be effectively treated by surgical removal of a portion of the cranium (craniectomy) to allow room for the brain to expand and the release of cerebrospinal fluid to reduce the increased pressure.

In the field of treatments for traumatic brain injury (TBI), the current practice in managing acute cases of medically uncontrolled brain swelling is to perform an emergency craniectomy. In this surgical procedure, a flap of cranium is removed from the patient's cranium in order to provide relief to intracranial pressure and reduce the risk of the aforementioned serious or fatal complications. In the established course of treatment, the initial craniectomy producing the cranial opening is followed by a period of intensive rehabilitation. During the entire recovery period, the cranium remains open, and must be shielded by protective head devices or coverings, and the patient's activities may be significantly restricted. The patient also runs a significant risk of infection and other post-surgical problems.

One serious problem that can arise during the post-operative period is the so-called Syndrome of the Trephined. This condition results from the sinking of the dura within the cranial opening due to the negative intracranial pressure relative to the atmospheric pressure which, induces derangements of cerebrospinal fluid flow, cerebral blood flow and brain metabolism, leading to psychological and/or physical deficits in the patient during the recovery period. Once the cranial opening is covered through a separate, later-stage procedure (cranioplasty), documented cases exhibiting the Syndrome of the Trephined have shown a reversal of these deficits with varying rates of improvement. However, the prevailing practice for performing a cranioplasty is to wait for an average of six months or longer after the emergency craniectomy before repairing the cranial opening.

The traditional approach of performing a two-staged procedure of an initial emergency craniectomy followed by a later cranioplasty can be attributed in part to a landmark study carried out by Rish et al. (see Rish, et al., Neurosurgery, 4:381-385, 1979) showing that a shorter time from craniectomy to cranioplasty leads to a poorer outcome. A closer examination of this study by other authors (see Carvi Y, et al., 2006 and Liang et al., 2007, below) however, showed that the cases in the Rish study only pertained to penetrating or open head injuries, ignoring cases of closed (non-penetrating) head injuries that needed decompressive craniectomies as well. In fact, these authors subsequently (see Carvi Y, et al., Neurol Res 28:139-144, 2006; Liang et al., J Craniofac Surg 18:526-532) reported good outcomes after early cranioplasty for non-penetrating head injuries.

Other scientific studies further support performing cranioplasties early after an emergency craniectomy. Data on wartime cranioplasty complications observed during the 2003-2008 Iraq-Afghanistan conflict period (see Stephens F L, et al., Neurosurgical Focus/Journal of Neurosurgery 28(5), 2010) show that the majority of infected cranioplasty cases occurred during a delayed period (90-270 days from injury/craniectomy). Furthermore, multivariate analyses cited the presence of cerebrospinal fluid leaks and repeated operations as the main independent risk factor for the development of craniotomy (brain operation) infections, and not the craniectomy-to-cranioplasty waiting period per se (see Korinek A M et al., Br. J Neurosurg 19:155-162, 2005 and Cheng Y K, et al., J Clin Neurosci 15:1115-1119, 2008).

Further evidence of the benefit of performing cranioplasty earlier after an emergency craniectomy is found from the analysis of craniotomies. In cases where the head-injured require the evacuation of hematomas (bleeding), immediate reinsertion of the skull flap (osteoplastic craniotomy) may be allowable if the result is a quiescent brain (non-edematous). When the intended skull flap has undergone multiple fracture sites and is deemed not to be viable by the neurosurgeon, the skull flap is replaced by commercially available cranioplasty materials (cranioplasty for craniotomies). Wartime data on cranioplasties done for craniotomies analyzed in the same study cited above (see Stephens F L, 2010) show a significantly lower infection rate, suggesting that the period when a cranioplasty procedure can expect the least infection rate would be during the time of the first procedure itself (initial craniotomy or craniectomy).

It follows that, for head injuries requiring an emergency craniectomy due to an edematous (swollen) brain, the optimal period for performing cranioplasty would be during the initial craniectomy. However, all currently available cranioplasty constructs, being rigid, are designed for a late-staged and/or delayed cranioplasty procedure and none are designed to accommodate the initial brain bulging and adapt to the brain movement until the brain contour (and swelling) could normalize. Despite evidence to the contrary and due to the absence of a cranioplasty construct for immediate application after emergency craniectomy, the prevailing practice of a delayed cranioplasty for those craniectomized head-injury patients persists.

It may be desirable to provide systems and methods for a cranial implant assembly adapted for insertion during craniectomy procedure, which, among other advantages, provide the ability to relieve swelling of the brain and dura after a brain trauma or injury by way of a craniectomy, while providing the opportunity to concurrently introduce a cranial implant construct or assembly, during the same initial procedure, with no second-stage surgery required.

DESCRIPTION OF THE DRAWINGS

The accompanying drawings, which are incorporated in and constitute a part of this specification, illustrate embodiments of the present teachings and together with the description, serve to explain the principles of the present teachings. In the figures.

SUMMARY

Embodiments of the present teachings relate to systems and methods for a cranial implant assembly adapted for insertion during a craniectomy procedure. More particularly, embodiments relate to an advanced cranial implant assembly which is capable of being introduced during the same surgical operation, procedure, or intervention as the craniectomy procedure performed to relieve pressure on swollen brain tissue or performed to correct a cranial malformation. The cranial implant assembly achieves a single-operation capability by having the ability to be introduced in an non-rigid state, and then to transition to a rigid overall state as the affected brain and/or dura returns to a normal shape.

These and other embodiments described herein address the various noted shortcomings in known cranial implant technology, and provide a physician, patient, or others with an enhanced treatment approach for TBI or other skull syndromes, deformities, and/or injuries in which both craniectomy and cranioplasty stages can be performed within a single or simultaneous surgical operation, procedure, or intervention.

DETAILED DESCRIPTION

Reference will now be made in detail to exemplary embodiments of the present teachings, which are illustrated in the accompanying drawings. Where possible the same reference numbers will be used throughout the drawings to refer to the same or like parts.

Figure 1:
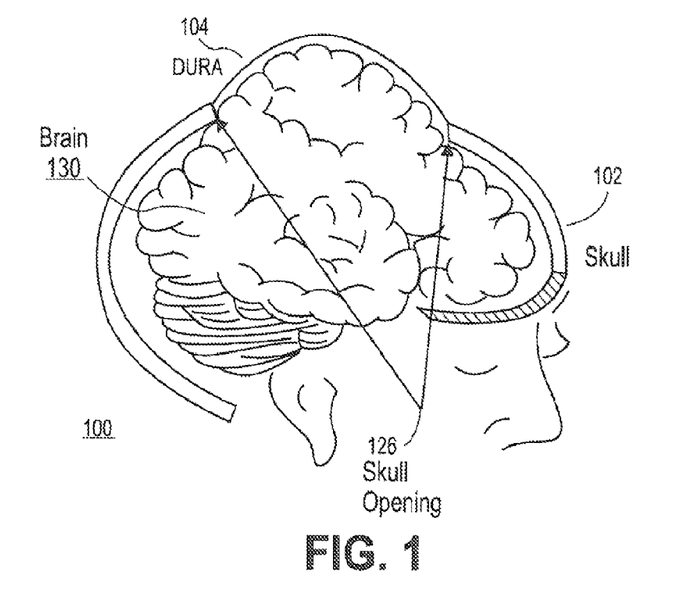
FIG. 1 illustrates side view of an overall surgical site in which reparative skull procedures using the inventive cranial implant assembly can take place, according to embodiments of the present teachings.

FIG. 1 illustrates a schematic diagram of a surgical site 100 in which systems and techniques according to the present teachings can be practiced. As shown, the surgical site 100 can comprise the head and/or skull area of a patient, in which the skull 102 of a patient is desired to be operated upon to produce a skull opening 126 exposing the underlying dura 104. The skull opening 126 can be produced using known techniques for performing a craniectomy, and therefore reduce the swelling, edema, inflammation, and/or pressure on the brain 130 and/or the dura 104 encapsulating the brain 130. In other instances, the skull opening 126 can be caused by a TBI itself.

Figure 2:
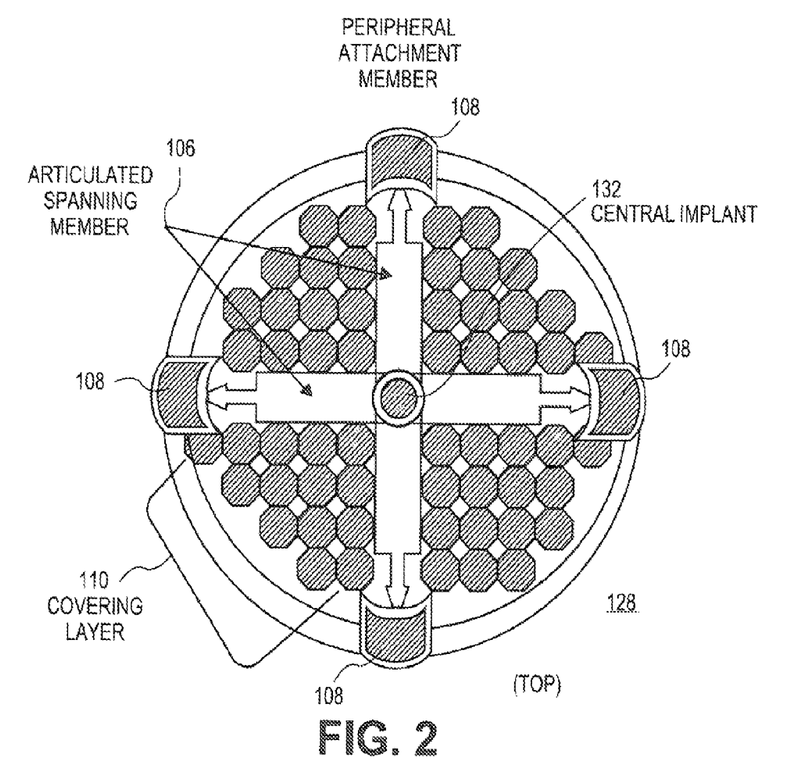
FIG. 2 illustrates an overall cranial implant assembly in a top view, according to various embodiments of the present teachings.

FIG. 2 illustrates a top view of a cranial implant assembly 128 according to aspects of the present teachings. In aspects, the cranial implant assembly 128 can, in general, be inserted or introduced in the area of the skull opening 126 as part of a concomitant cranioplasty procedure that can take place simultaneously with the craniectomy used to produce the skull opening 126. As used herein, two or more procedures or actions performed "simultaneously" means procedures performed at the same time, at closely separated times, and/or during the same overall surgical operation, procedure, and/or intervention. In aspects, "simultaneously" can refer to craniectomy, cranioplasty, and/or other procedures of actions performed within 24 hours of each other, or procedures separated by smaller or larger intervals of time.

In embodiments as shown, the cranial implant assembly 128 can, in general, comprise a number of components, elements, or constructs which cooperate to provide an expansile, elastic, semi-rigid, or flexible protective structure over the skull opening 126 during an initial period after the opening of the skull opening 126. As used herein, "semi-rigid" means any state less rigid than a state of full or maximally attainable rigidity. The cranial implant assembly 128 can, however, retain the ability to gradually transition to a rigid state, as the swelling of the brain 130 and/or dura 104 subsides during the post-operative phase.

In aspects as shown, the cranial implant assembly 128 can comprise generally shallow hemispherical construction, including an articulated spanning member 106 (or similar bridging scaffold) which spans the skull opening 126 and forms a topmost structural element, which provides protection and support to the cranial implant assembly 128. In embodiments as shown, the articulated spanning member 106 can comprise a pair of bridging crossarms, which act as a scaffold-like structure above the skull opening 126. In embodiments as shown, the crossarms are arranged generally perpendicular to each other, so that the two crossarms form a general X shape that extends across the skull opening 126. It will however be appreciated that other types, shapes, or constructions of the articulated spanning member 106 can be used.

In general, the articulated spanning member 106 can be introduced into the area of the skull opening 126 in a non-rigid or semi-rigid, expansile, elastic, or flexible state. That expansile or elastic state can be achieved for instance using separated or articulated sub-elements held together, for example, with a guide wire, as described further herein. The articulated spanning member 106 can likewise comprise a central implant 132, located, for instance as shown, in the center of the articulated spanning member 106. In aspects, the central implant 132 can attach or connect to the underlying dura 104, and create a point of rigid connection to the dura 104, serving as a guide post from which the cranial implant assembly 128 will arrange itself on the skull defect and adapt to brain swelling and its resolution.

According to embodiments as shown, the cranial implant assembly 128 can likewise comprise a cover 110, configured to be generally disposed underneath the articulated spanning member 106. In embodiments as shown, the covering layer 110 can comprise a set of "chain-mail"—like quadrants of expansile or flexible subunits that can be held together, for example, with a set of guidewires to create a relatively flexible mesh, sheet, membrane, layer, and/or other covering construct.

The cranial implant assembly 128 can also comprise a peripheral attachment member 108 (or similar peripheral implant) that is configured to be attachable to the articulated spanning member 106. In embodiments as shown, the peripheral attachment member 108 can consist of a ring-like or annular structure that is capable of being connected or attached to the bone edges of the skull opening 126, for instance, using surgical screws or other techniques known to those skilled in the art. In aspects, the tips or ends of the articulated spanning member 106 can be generally aligned with the peripheral attachment member 108. The articulated spanning member 106 and the peripheral attachment member 108 can be configured with a mutual locking mechanism, which permits those to elements to move into registration with each other, and to attain a rigid state. Any locking or registration mechanism known in the art can be used. In embodiments, the locking mechanism can consist of mutually aligned magnets, which attract and lock the articulated spanning member 106 and peripheral attachment member 108 when they reach sufficient proximity to each other. This registration occurs as the swelling of the dura 104 and/or brain 130 subsides, and the recession of the dura 104 begins to pull the articulated spanning member 106 in a downward direction, in embodiments shown, for example, in FIG. 2, the peripheral attachment member 108 can comprise four units that are configured to register into place with their ends to the ends of the two bridging crossarms. It will however be appreciated that while particular constructions of the cover 110 and the peripheral attachment member 108 are shown, other types, shapes, and constructions of those elements can likewise be used.

According to aspects, and also in general, the cranial implant assembly 128 can, due to the cooperation of its various elements, remain in a non-rigid, expansile, or elastic state when first implanted simultaneously with the craniectomy used to produce the skull opening 126. In this state, both the articulated spanning member 106 and the underlying cover 110 can remain in a flexible state, in aspects because the position of the swollen dura 104 exerts pressure on those elements to remain in an expansile or elastic state. In that condition, the guidewire or other meshing mechanism used to generally align those structures remains relatively loose, and the articulated spanning member 106 and peripheral attachment member 108 do not descend or significantly descend to a lower level relative to the skull opening 126.

However, as shown for instance in FIG. 2, as swelling in the dura 104 and/or brain 130 begins to significantly subside, the dura 104 can begin to recede toward the skull opening 126. In aspects, the reduction in swelling in the dura 104 and/or brain 130 can be expected to begin to take place within a few days to a few weeks of time after implantation of the cranial implant assembly 128, although the response of each individual patient will be different. In embodiments, the exertion of a downward-pulling force by the receding dura to the central implant 132 attached to the dura 104 can begin to cause a lateral force or tension to be exerted on a guidewire 116 in the articulated spanning member 106. Particularly, the guidewire can begin to tighten a set of subunits 124 of the articulated spanning member 106, placed next to each other and connected through the guidewire 116 to form the articulated spanning member 106, in articulated fashion.

Figure 3:
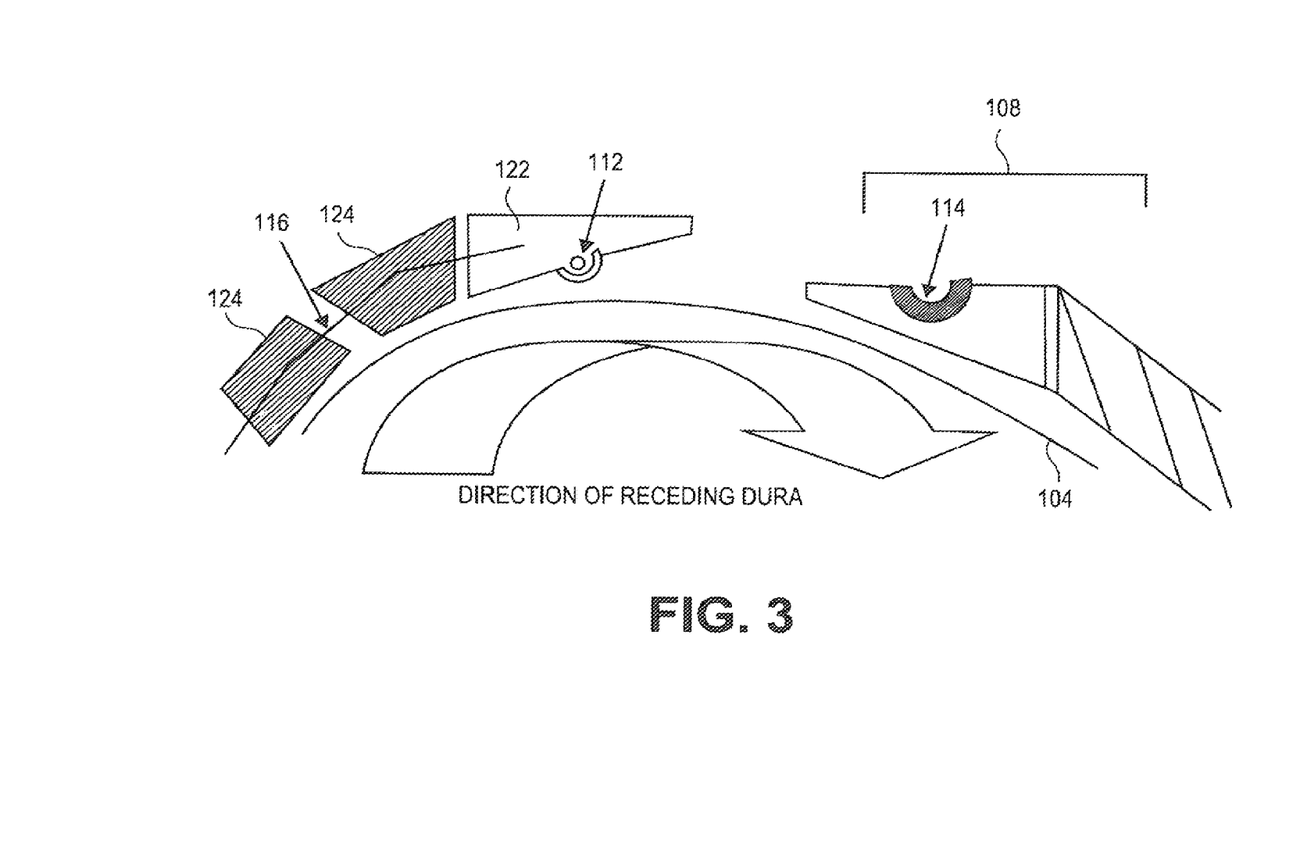
FIG. 3 illustrates a side view of the cranial implant assembly of the present teachings undergoing a displacement due to recession of the patient dura, according to various embodiments.

The individual subunits of the set of subunits 124 can be of any shape provided they are capable of transitioning from an expansile and/or semi-rigid state to a rigid state as the swelling of the dura 104 and/or brain 130 subsides. In embodiments, the subunits of the set of subunits 124 can be formed to have a width of approximately one-fifth of the length of each arm of the articulated spanning member 106, or can have other sizes or dimensions. As shown, for instance, in FIG. 3, as the guidewire 116 tightens the set of subunits 124, a terminal subunit 122 of the set of subunits including a magnet 112 can be drawn into proximity of a magnet 114 embedded in the peripheral attachment member 108. Within a certain small distance, the strength of the magnetic field between magnet 112 and magnet 114 will be sufficient to lock the terminal subunit 122 into place with the peripheral attachment member 108, and create a fixed, rigid, and/or permanent attachment or connection between the overall articulated spanning member 106 and the peripheral attachment member 108. As this registration or locking action takes place, the cover 110 is also drawn or pressed into a position where the subunits of the cover 110 are brought into contact with each other to interdigitate, or also lock into place.

Figure 4A:
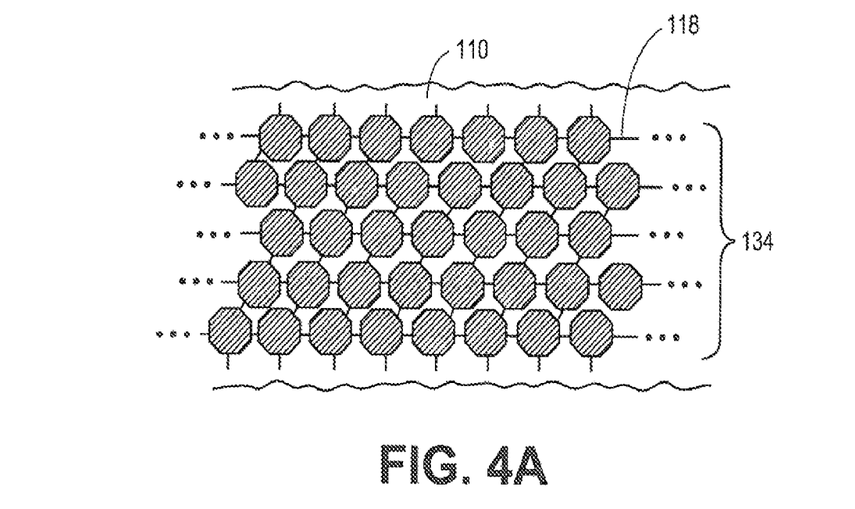
FIG. 4A illustrates a top view of a set of interdigitating subunits for a cover of the cranial implant assembly, according to various embodiments.
Figure 4B:
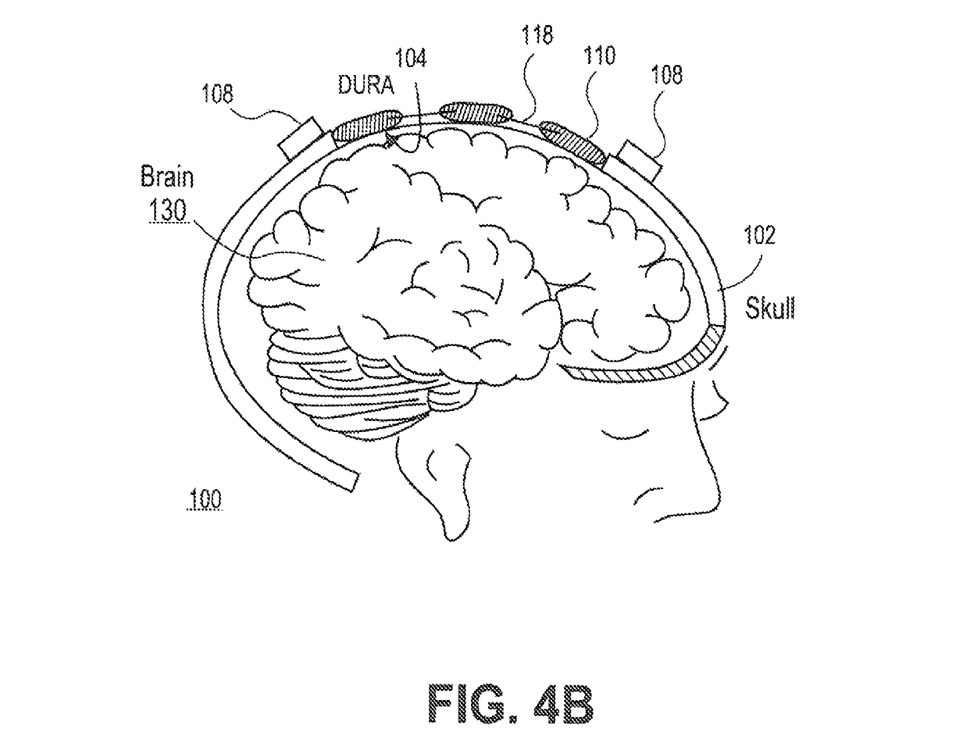
FIG. 4B illustrates a side view of a set of interdigitating subunits for a cover of the cranial implant assembly, according to various embodiments.

More particularly, and as for instance shown in FIG. 4A, the cover 110 can comprise a set of interdigitating subunits 134 connected by a set of guidewires 118. The set of guidewires 118 can be or include a set of wires arranged in a generally crossed or cross-hatched pattern through the rigid subunits of the set of interdigitating subunits 134. In aspects, and as shown for instance in FIG. 4B, the set of interdigitating subunits 134 can, again, remain in an expansile, elastic, semi-rigid, or flexible state in a type of "ripped skirt" configuration. The expansile or semi-rigid state can persist until the tension exerted on the set of interdigitating subunits 134 through the set of guidewires 118 due to the downward force of the articulated spanning member 106 being pulled toward the skull opening 126 by the central implant 132 attached to the receding dura 104 begins to draw those subunits together. The individual subunits of the set of interdigitating subunits 134 can be formed with interdigitating clasps, clips, and/or other structures to bind together once brought into contact with each other. The rigid subunits of the set of interdigitating subunits 134 can thereby lock into place and thus produce a rigid state in the cover 110 as illustrated in FIG. 4A, after sufficient tension through the set of guidewires 118 has been applied.

In embodiments, it may be noted that the individual subunits of the set of interdigitating subunits 134 can be sized to be approximately one-eighth the size of each quadrant of the cover 110, or can in embodiments be of other sizes or dimensions. It may be noted, again, that after a rigid state of the cover 110 has been achieved, both the articulated spanning member 106 and the cover 110 are now in a mechanically or structurally fixed or rigid state, providing a dome or helmet-like structure for protection of the dura 104 and brain 130. This protective rigid construct is thus achieved without a necessity for a second surgical procedure, but instead, relying upon the ability of the cranial implant assembly 128 to transition from an expansile or elastic state to a rigid state, without further intervention after the initial implantation of the construct.

Figure 5A:
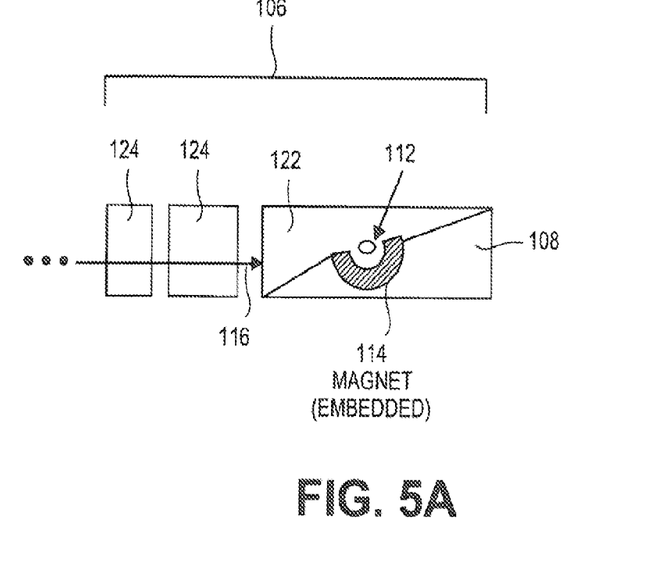
FIG. 5A illustrates a side view of a magnetic locking mechanism that can be used to lock an articulated spanning member and peripheral attachment member, according to various embodiments.

In the eventual rigid state achieved in the articulated spanning member 106 and cover 110, the articulated spanning member 106 can register into a locked and permanent position with the peripheral attachment member 108, as for instance shown in FIG. 5A. In embodiments as shown, the terminal subunit 122 of the set of subunits 124 can slide into place on a planar face or circumferential edge of the peripheral attachment member 108. In aspects, the terminal subunit 122 and the circumferential terminal subunit 120 can be formed with angled or chamfered edges that slide into mating position with each other. In that position, the magnet 112 and the magnet 114 are located in relatively close proximity to each other, allowing magnetic attachment or locking to take place. It will be appreciated that other registration and locking mechanisms between the articulated spanning member 106 and peripheral attachment member 108 be used, in addition to or instead of a magnetic mechanism as illustrated.

Figure 5B:
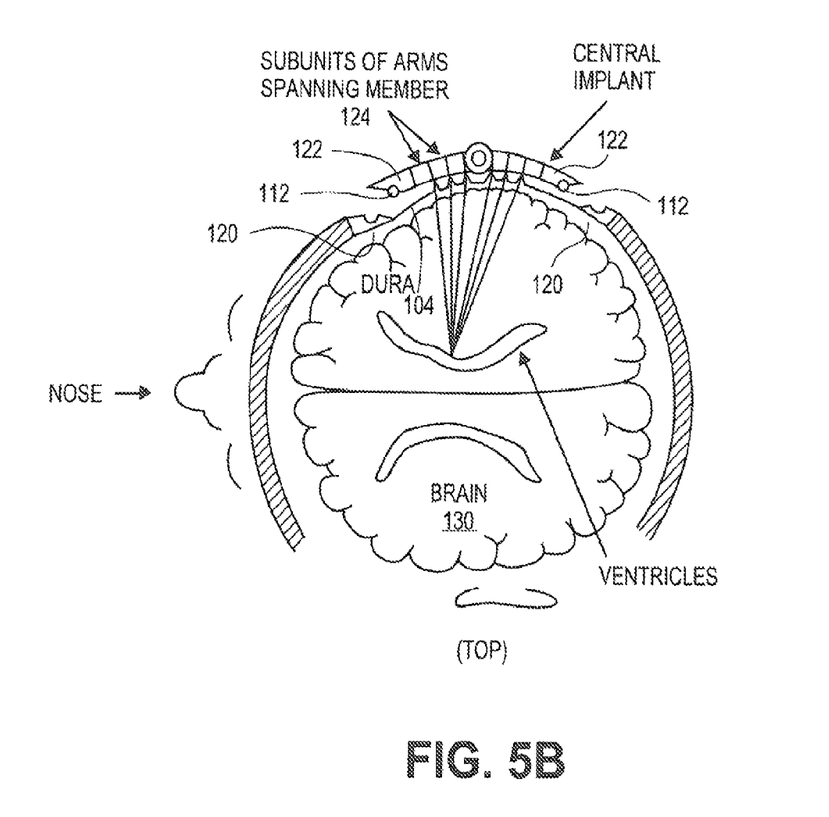
FIG. 5B illustrates a diagram of sizing and other computations that can be carried out, according to various embodiments of the present teachings.

In terms of the sizing, fitting, and placement of the cranial implant assembly 128 and its various components in the intended surgical site, it may be noted that the area required to be covered by the cranial implant assembly 128 can be computed according to the diagram shown in FIG. 5B. In aspects, the overall size, shape, and curvature of the patient's skull 102 can be determined by magnetic resonance imaging (MRI) or other imaging techniques. The intervening surface area, or gap, between the peripheral attachment member 108 and cover 110 can vary according to the degree of edema, distension, or swelling of the dura 104 from its normal position within the skull 102. The desired endpoint is always to replicate the normal curvature of the skull 102. In connection with this fitting of the cranial implant assembly 128 to the skull 102 including the skull opening 126, areas of interest can be calculated per the following.

$$A_3 = A_1 - A_2 \quad \text{Equation 1}$$

$$A_1 = (\pi r^2_1)/2 \quad \text{Equation 2}$$

$$A_2 = (\pi r^2_2)/2 \quad \text{Equation 3}$$

$$r_3 = r_1 - r_2. \quad \text{Equation 4}$$

In the preceding equations, $A_1$ represents the area of the dura 104 with swelling, $A_2$ represents the area of the dura 104 in normal curvature, and $A_3$ represents the area of the gap. Likewise, $r_1$ represents the radius of the area of the dura 104 with swelling, and $r_2$ represents the radius of the area of the dura 104 without swelling.

After computation of the correct fitting of the cranial implant assembly 128 to the intended surgical site, the cranial implant assembly 128 can be fabricated by automated and/or mechanically assisted techniques, including stereolithography. It may be noted that in embodiments, one or more components of the cranial implant assembly 128, or the entire cranial implant assembly 128, can be fabricated from titanium, stainless steel, bioceramic, and/or other materials. As shown in FIG. 5B, the cuts of the set of subunits 124 can be determined by a line drawn from a middle portion of the underlying brain ventricles or canals which bisects the subunits as they cross the curvature of the overlying dura 104.

It may also be noted or more components of the cranial implant assembly 128, or the entire cranial implant assembly 128, can be coated with an antibiotic to assist in reducing the risk of infection in the surgical site 100. Likewise, in embodiments, one or more components of the cranial implant assembly 128, or the entire cranial implant assembly 128, can be coated or covered with osteoconductive periosteum, and/or other growth-promoting material, to promote the growth of replacement skull material in the skull opening 126 over the cranial implant assembly 128.

Figure 6:
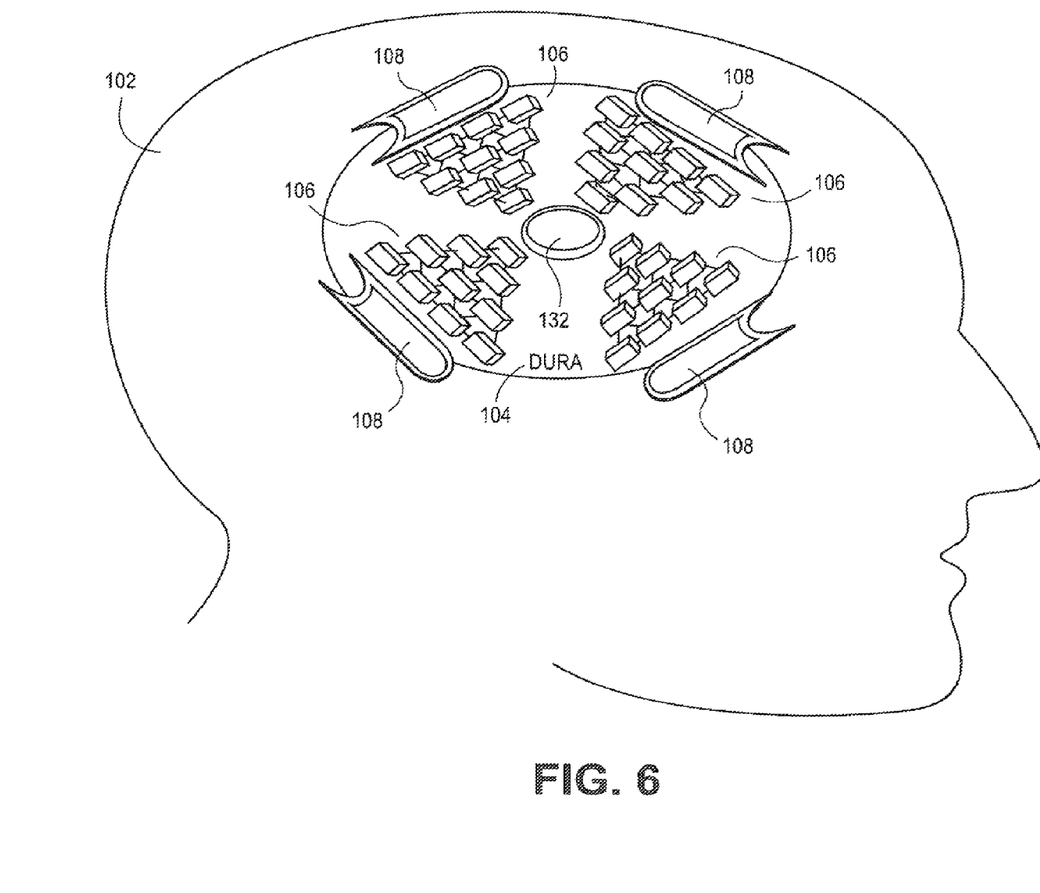
FIG. 6 illustrates aspects of a cranial implant assembly, according to further embodiments.

It may likewise be noted that although embodiments have been described above in which the cranial implant assembly 128 is configured to include an articulated spanning member 106 consisting of two (generally perpendicular) rectangular elongated crossarms, the articulated spanning member 106 can, in embodiments, be constructed in other configuration. For example, in embodiments as shown in FIG. 6, the articulated spanning member 106 can be constructed as a pair of elements formed in a tapered or pyramid-like shape, with the base of the elements formed nearest to the edge of the skull opening 126. In embodiments as shown in that figure, an expansile state can likewise be achieved using guidewires or other connective mechanisms.

While embodiments have also been described above in connection with a surgical site 100 involving a patient skull 102, it may be noted in embodiments, the constructs of the present teachings can be adapted to other surgical applications. Aside from the treatment of traumatic brain injury (TBI), decompressive craniectomy, in its objective to relieve intracranial pressure, has been used in other conditions where efforts to control brain swelling medically have failed. As such, in the past, the initial emergency decompressive craniectomy has predisposed the provider to plan for an eventual late-staged cranioplasty, due to the absence of a construct that can be applied during the time of the emergency craniectomy, such as constructs according to the present teachings.

Among the further conditions to which implants according to the present teachings can be applied include "malignant" cerebral infarction. Cerebral infarction is a type of "stroke" (used herein as a general or umbrella term) whereby the blood supply to a major part of the brain becomes occluded and results in brain swelling. The term "malignant" as it is alluded to in the medical sense has been applied here to mean cerebral infarction which is refractory to medical treatment, and for which a surgical option (decompressive craniectomy) is recommended to avoid a fatal outcome. The multicenter pooled European randomized controlled trials (Decimal, Destiny, Hamlet, March, 2007) on application of decompressive craniectomy (DC) for malignant infarction of the middle cerebral artery (MCA) reported deconstructive craniectomy being beneficial for all the subgroups examined, resulting in recommendations for applying deconstructive craniectomy for malignant infarction emanating from US and European neurosurgical, neurological and cardiovascular professional societies. Upon survival, all craniectomized infarcted patients will need an eventual cranioplasty for cosmesis, brain protection and treatment of cerebrospinal fluid and cerebral perfusion disorders stemming from the craniectomy.

Further applications for constructs according to the present teachings include the treatment of brain tumors. One of the earliest uses of deconstructive craniectomy was documented by Dr. Harvey Cushing (the historically accepted father of neurosurgery) when he used deconstructive craniectomy in relieving severe cerebral edema caused by tumor removal in the brain in 1901. Cerebral swelling after tumor removal has not been an uncommon occurrence since the brain's vascular architecture, long displaced by a slow-growing tumor, usually reacts to tumor removal by going into vasospasm (reflex vessel constriction) causing diminished blood flow to the brain and consequent brain swelling. Excision of some parts of the brain may also be necessary to get to the tumor and this ablative aspect of tumor surgery itself can cause brain swelling. Upon rehabilitation, post-craniectomy cranioplasty is sought for these patients for similar purposes as described herein.

Additional applications for constructs according to the present teachings include epilepsy surgery. One type of seizure surgery is usually ablative, meaning a part of the diseased brain which is proven to be epileptogenic (causing seizures) is excised. The brain normally reacts to injury (ablative surgery) by swelling, which is relieved by deconstructive craniotomy. Second-stage cranioplasty is then required.

Figure 7:
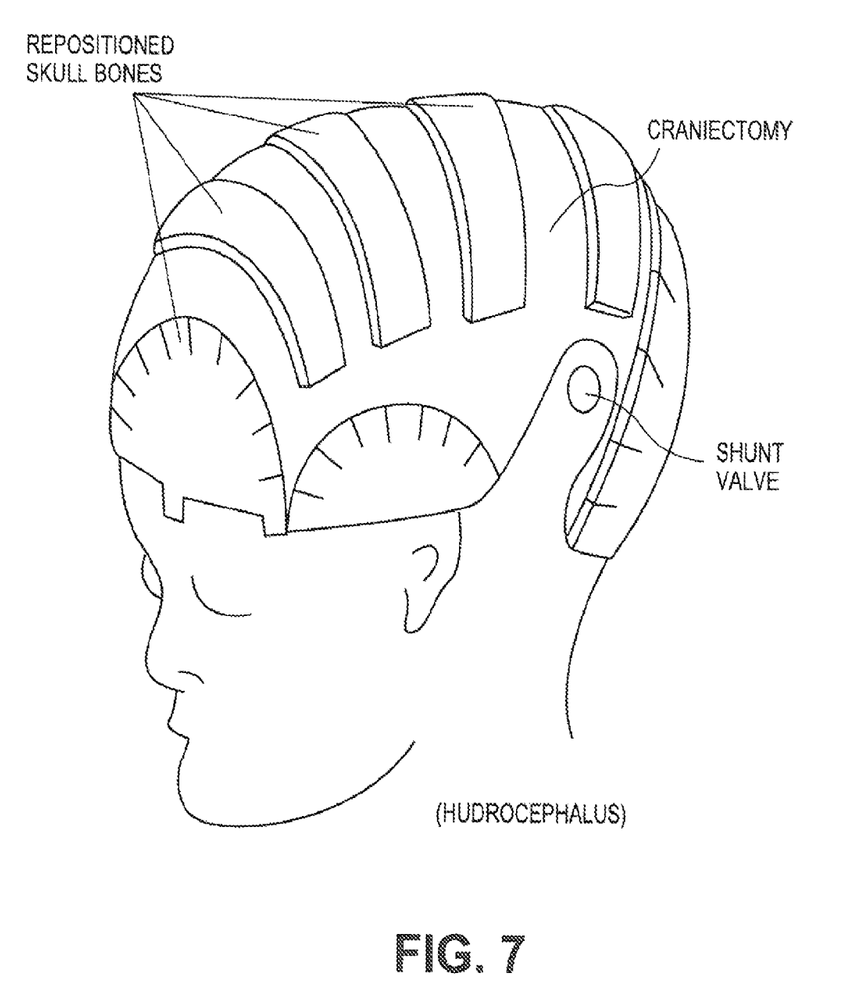
FIG. 7 illustrates conventional craniectomy treatments that have been used in connection with cases of hydrocephalus.

Still further applications for constructs according to the present teachings include the treatment of craniosynostosis—a general term for congenital anomalies causing misshapen skulls, referring to premature fusion of the skull sutures. The cranium has suture lines separating the bony plates of the skull which later fuse as the child undergoes skull molding during growth. Suture lines may prematurely fuse or even fuse asymmetrically, causing a misshapen skull. The final skull shape will depend on which suture line(s) prematurely fuse. Those various conditions or deformities are given descriptive names ending with -"cephaly," e.g. scaphocephaly (canoe-head), brachycephaly (clover-leaf head), turricephaly (tower skull), etc. Correction and repair of these misshapen skulls require partial or full craniectomy for purposes of cosmesis (to address social dysfunction), impending mental retardation, or impending visual problems caused by shifting intracranial pressure rises due to the misshapen skull. FIG. 7 illustrates conventional treatment of an enlarged cranial vault in a child with hydrocephalus, in which a craniectomy is performed to produce multiple separated skull sections. In this conventional approach, a shunt valve may also be introduced to assist in reducing intracranial pressure.

Figure 8:
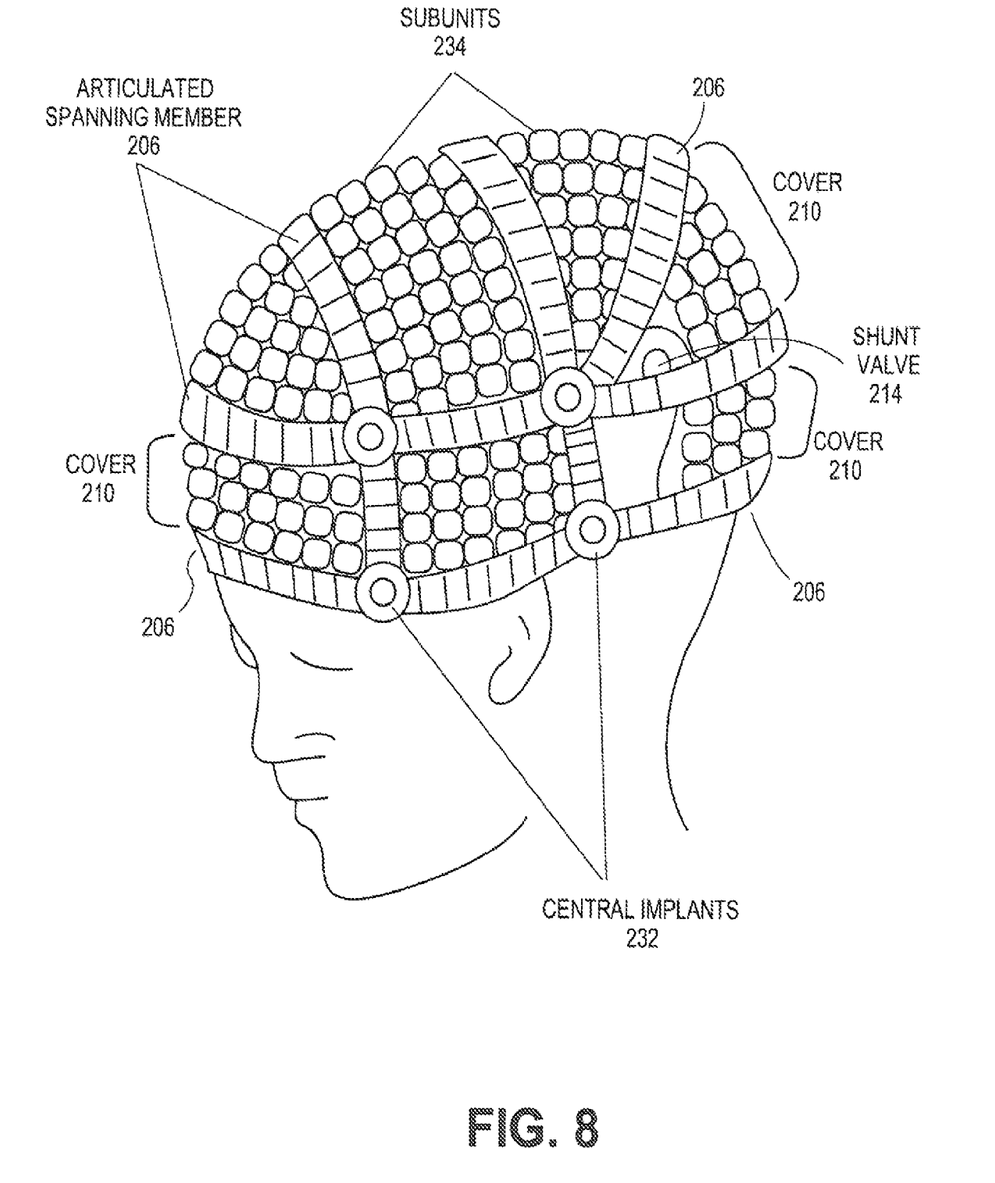
FIG. 8 illustrates a cranial implant that can be used in connection with the treatment of cases of hydrocephalus, according to various embodiments.

FIG. 8 illustrates a cranial implant assembly 228 that may be directed to the treatment of children having hydrocephalus, according to further various embodiments of the present teachings. In embodiments as shown, the pediatric patient can have an enlarged cranial vault due to the effects of hydrocephalus. In embodiments as shown, the cranial implant assembly 228 can comprise an articulated spanning member 206 whose multiple guide arms are snugly applied in strap-around fashion to the patient skull, to produce surgical skull shape correction. A set of central implants 232 can be attached or connected to the underlying dura (not shown), which set of central implants 232 serve to hold a cover 210 in place over the various skull openings or fissures produced by the multipart or multi-section craniectomy. The cover 210 can comprise a multi-part expansile, flexible, and/or semi-rigid cover or layer each section of which has a set of subunits 234, which can be a set of interdigitating subunits similar to those described in embodiments above. The set of subunits 234 can be connected via a set of guidewires (not shown) in articulated fashion, likewise as above. In aspects, the cranial implant assembly 228 can be configured to transition to an eventual rigid state through the tensioning and locking of the cover 110 and articulated spanning member 206 to a magnetic peripheral member (not shown) or other attachment site, in a manner generally similar to or using mechanisms like those described above. In aspects, a shunt valve 214 may also be inserted to assist in regulating intracranial pressure. Various embodiments of the present teachings including those shown in FIG. 8 will expedite the usually long period of operation needed in repairing the skull anomalies in pediatric patients, a vulnerable group. Some of the types of craniosynostosis that can be treated using these inventive constructs are part of a syndrome known by different names (Crouzon's syndrome, etc.).

According to yet further aspects, embodiments of the constructs of the present teachings can be used to treat other skull shape anomalies which are not congenital, but which may still require deconstructive cranietomy for repair. Those anomalies include positional ones, such as plagiocephaly (flat-headed condition) that is usually caused by poor child care when the child is left on the supine position for a long time, and the back head is positioned against a flat firm surface Those anomalies likewise include hydrocephalic megacephaly, or the condition of a large skull for infant/child's size caused by an underlying hydrocephalus (cerebrospinal fluid, or CSF disorder) where the amount of CSF produced is not absorbed by the body but accumulates in the brain. This results in a relatively rapid increase in skull size and separation of the still unfused suture lines. Aside from a shunting procedure which diverts the accumulated CSF for absorption, a cranial vault reduction cranioplasty is done to correct skull shape. Constructs according to embodiments of the invention may expedite repair in this condition, as well.

It will again, however, be appreciated that surgical constructs according to embodiments of the present teachings, and/or adaptations of those constructs, can be used in even further applications, including to treat other cranial conditions besides those directly noted herein, and/or to treat and heal conditions of other bone structures, tissues, organs, and/or areas of the body.

The foregoing description is illustrative, and variations in configuration and implementation may occur to persons skilled in the art. For example, while embodiments have been described in which the articulated spanning member 106 consists of two generally perpendicular crossarms or other structural elements, in embodiments, three, four, and/or other numbers or crossarms can be used, for instance, divided in a hemispherical pattern or arrangement over the skull opening 126. For further example, while embodiments have been described in which the cover 110 is sub-divided into four quadrants or regions, in embodiments, the cover 110 can be divided into other numbers or types of sections or regions. Other elements or resources described as singular or integrated can in embodiments be plural or distributed, and elements or resources described as multiple or distributed can in embodiments be combined. The scope of the present teachings is accordingly intended to be limited only by the following

What is claimed is:

1. A cranial implant assembly, comprising:
an articulated spanning member, the articulated spanning member comprising a central implant and being configured to—
be attachable in a non-rigid state, via the central implant, to an area of swollen dura exposed in a skull opening,
be attachable to a peripheral area of the skull opening, and
remain in a non-rigid state before being attached to the peripheral area of the skull opening;
a cover, configured to—
be disposed below the articulated spanning member, and
provide a non-rigid covering over the skull opening while the articulated spanning member is in a non-rigid state; and
a peripheral attachment member, configured to be attached to the peripheral area of the skull opening;
wherein the articulated spanning member is configured, after swelling of the dura subsides, to—
register into place at the peripheral attachment member, and enter a rigid state; and
wherein the cover is configured to transition to a rigid state as the articulated spanning member registers into place at the peripheral attachment member.

2. The cranial implant assembly of claim 1, wherein the articulated spanning member comprises at least two crossarms, with each crossarm having a first end and a second end, wherein the first end and the second end are configured to be attachable to the peripheral attachment member.

3. The cranial implant assembly of claim 2, wherein the at least two cross arms are arranged at least approximately perpendicular to each other.

4. The cranial implant assembly of claim 2, wherein each of the crossarms comprises a set of articulated subunits.

5. The cranial implant assembly of claim 4, wherein the set of articulated subunits are articulated via a guide wire.

6. The cranial implant assembly of claim 2, wherein
the first and the second end of each of the crossarms comprises a magnetic tip, and
the peripheral attachment member comprises a set of magnets configured to register with respective magnetic tips of the crossarms.

7. The cranial implant assembly of claim 6, wherein the articulated spanning member transitions from a non-rigid state to a rigid state due to—
the magnetic tips of the crossarms locking into place with the set of magnets on the peripheral mounting member, and
tension being applied to the guide wire as a result of the magnetic tips of the crossarms locking into place.

8. The cranial implant assembly of claim 7, wherein the cover comprises a set of covering subunits, wherein the covering subunits are configured to interdigitate with each other due to pressure exerted by the articulated spanning member transitioning to a rigid state.

9. The cranial implant assembly of claim 8, wherein the set of covering subunits comprises at least four quadrants of covering subunits aligned below the crossarms.

10. The cranial implant assembly of claim 9, wherein the set of covering subunits are connected via a set of guide wires.

11. The cranial implant assembly of claim 2, wherein the articulated spanning member is made of at least one of titanium, stainless steel, or bioceramic material.

12. The cranial implant assembly of claim 2, wherein the cover comprises an antibiotic coating.

13. The cranial implant assembly of claim 2, wherein the cover comprises a periosteum coating.

14. A method of introducing a cranial implant assembly in a subject, comprising:
performing a surgical procedure to produce a skull opening in the subject; and
introducing the cranial implant assembly of claim 2 to cover the opening, wherein the cranial implant assembly is introduced simultaneously with the surgical procedure.

15. The method of claim 14, wherein the cranial implant assembly is introduced in connection with the treatment a traumatic brain injury in the subject.

16. The method of claim 14, wherein the cranial implant assembly is introduced in connection with the treatment of a congenital skull defect in the subject.

17. The method of claim 14, wherein the cranial implant assembly is introduced in connection with the treatment of a non-congenital skull defect in the subject.

18. The method of claim 14, wherein the cranial implant assembly is introduced in connection with the treatment of a stroke experienced by the subject.

19. The method of claim 14, wherein the cranial implant assembly is introduced in connection with the treatment of a tumor in the subject.

20. The method of claim 14, wherein the cranial implant assembly is introduced in connection with the treatment of an epileptic condition experienced by the subject.

* * * * *